US006446515B2

(12) United States Patent
Cole et al.

(10) Patent No.: US 6,446,515 B2
(45) Date of Patent: Sep. 10, 2002

(54) SAMPLING DEVICE

(75) Inventors: Alun Cole; Elizabeth Angela Woolfenden, both of Bridgend (GB)

(73) Assignee: Markes International Limited, Mid Glamorgan (GB)

( * ) Notice: Subject to any disclaimer, the term of this patent is extended or adjusted under 35 U.S.C. 154(b) by 0 days.

(21) Appl. No.: 09/855,184

(22) Filed: May 14, 2001

(30) Foreign Application Priority Data

May 17, 2000 (GB) .............................. 0011729

(51) Int. Cl.[7] ................................. G01N 1/00
(52) U.S. Cl. ................................. 73/863.21
(58) Field of Search ............... 73/863.21, 863.23, 73/863.33, 864.51, 864.91, 864.23–864.25

(56) References Cited

U.S. PATENT DOCUMENTS 4,478,095 A * 10/1984 Bradley et al. .......... 73/864.23
5,517,866 A * 5/1996 Manning et al. ......... 73/863.21
5,898,114 A * 4/1999 Basch et al. ............. 73/863.23

FOREIGN PATENT DOCUMENTS

| DE | 196 21 179 A1 | 11/1997 |
| DE | 196 46 994 A1 | 5/1998 |
| DE | 197 23 627 A1 | 12/1998 |
| DE | 299 07 313 U1 | 9/1999 |
| EP | 0676630 A1 | 10/1995 |
| EP | 0816823 A1 | 1/1998 |
| EP | 0875292 A1 | 11/1998 |

* cited by examiner

Primary Examiner—Robert Raevis
(74) Attorney, Agent, or Firm—Edwin D. Schindler

(57) ABSTRACT

A sampling device comprising an elongate tube and an identification device. The identification device comprises a transponder which is removably attached to the tube by means of a clip. The identification device may thus be removed from the tube prior to analysis and/or replaced between successive sampling operations.

33 Claims, 1 Drawing Sheet

SAMPLING DEVICE

BACKGROUND OF THE INVENTION

1. Field of the Invention

The present invention relates to a device for sampling atmospheric conditions at a test location for subsequent analysis.

2. State of the Art

It is known to provide a sampling device in the form of an elongate tube containing a quantity of adsorbing material. At least one end of the tube is provided with a removable cap which allows the interior of the tube, once exposed to the surrounding atmosphere at a test site, to be sealed prior to the analysis of its contents.

Analysis of the contents of the tube involves removing the cap from the end of the tube, applying heat to the tube to release adsorbed substances from the adsorbing material and driving the released substances out of the tube using a flow of gas.

However, a difficulty arises in labelling such tubes, in a convenient manner, such that they may be readily distinguished from one another at an analysis site and such that the tubes may be subsequently re-used.

We have now devised an arrangement which overcomes the limitations of existing sampling devices.

SUMMARY OF THE INVENTION

In accordance with the present invention, there is provided a sampling device comprising an elongate tube and an identification device comprising a transponder which is removably attached to the tube by means of a clip.

The identification device may thus be removed from the tube prior to analysis and/or replaced between successive sampling operations.

Preferably the transponder is attached to the tube such that it does not directly contact the exterior surface of the tube. The transponder is thus thermally isolated from the tube to a substantial extent, thereby allowing the identification device to remain attached to the tube during analysis.

Preferably the tube is formed with a reduced diameter portion within which the clip is attached to inhibit movement of the identification device along the length of the tube.

Preferably the reduced diameter portion is situated towards one end of the elongate tube, so that the opposite end of the tube may be heated during analysis without damaging the transponder.

Preferably the clip comprises a first part for attaching to the tube and a second part for attaching the transponder to the first part, thereby allowing a spent transponder to be readily replaced without sacrificing the clip.

Preferably the first part comprises a pair of resilient arms which engage opposite sides of the tube and connecting portions which extend between the two arms at spaced apart points along the axis of the tube, with the second part comprising a generally U-shaped member which clips around the transponder and the two connecting portions of the first part to hold the transponder against the undersides of those portions. The transponder is thus substantially encapsulated, with the gap between the two connecting portions providing a window through which the transponder may be read.

Preferably the resilient arms are arcuate in form and engage the sides of a cylindrical tube.

The clip, or at least the first part of the two part clip described above, is preferably formed from a material having low thermal conductivity, thereby further thermally isolating the transponder from the tube.

The sampling tube may be formed from glass or from a metallic material.

Also in accordance with the present invention, there is provided an identification device comprising a transponder and a clip for attaching the transponder to an elongate sampling tube.

Further in accordance with the present invention, there is provided a method of labelling a sampling tube comprising removably attaching a transponder to the tube by means of a clip.

An embodiment of the present invention will now be described by way of an example only and with reference to the accompanying drawings, in which:

DETAILED DESCRIPTION OF THE PREFERRED EMBODIMENT

Figure 1:
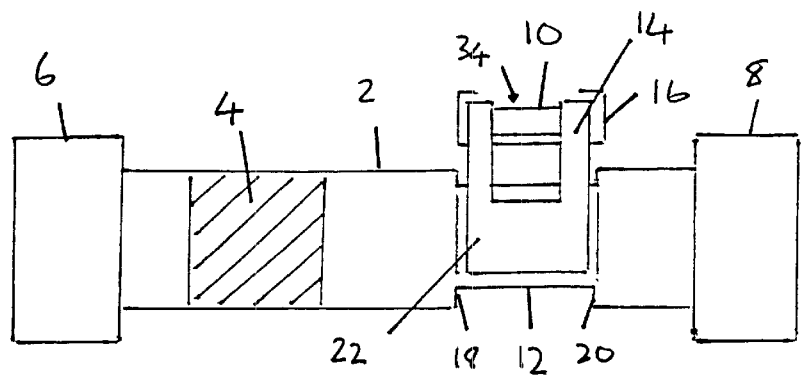
FIG. 1 is a side elevation of a sampling device in accordance with the present invention.
Figure 2:
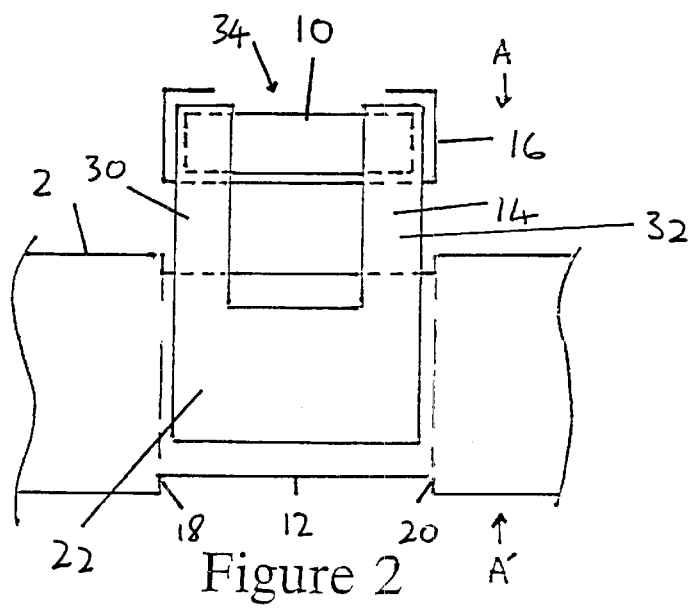
FIG. 2 is an enlarged side elevation of a portion of the device of FIG. 1.

Referring to the drawings, a sampling device is shown comprising an elongate cylindrical glass tube 2 containing a quantity of adsorbing material 4, the opposite ends of the tube 2 being closed by removable end-caps 6,8.

To acquire an atmospheric sample at a test location, the end-caps 6,8 are first removed from the tube 2 for a pre-determined period of time and then replaced to prevent contamination of the sample. The caps 6,8 are once again removed for analysis of the sample, which requires the tube 2 to be heated to approximately 250° C. to release adsorbed substances from the adsorbing material 4 into a flow of inert gas through the tube.

An identification device in the form of a generally flat, rectangular transponder 10 is removably attached to a reduced diameter portion 12 at one end of the tube 2 by means of a two-part clip 14,16, the side-walls 18,20 of the reduced diameter portion 12 acting to prevent the clip 14,16 from sliding along the tube. The transponder 10 may, for example. be programmed with a unique identification code or with data relating to the sample contained within the tube 2, for subsequently identifying or processing the sample.

Figure 3:
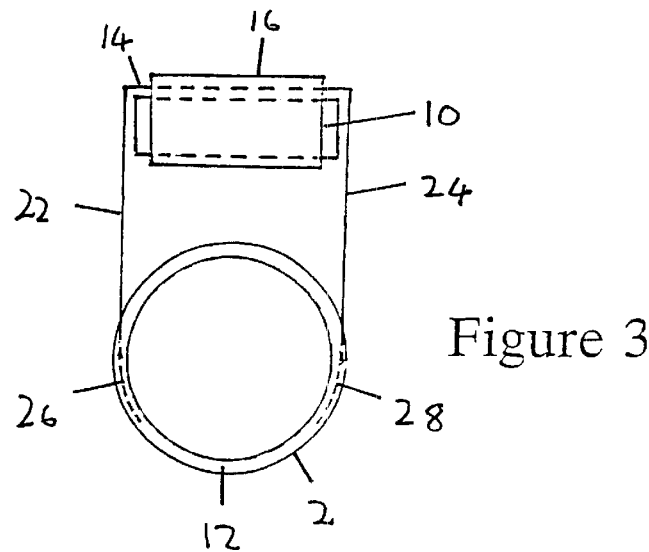
FIG. 3 is a sectional view through the device of FIG. 1 along the line A,A'.

The first part 14 of the clip comprises a pair of resilient arms 22,24 formed with arcuate distal ends 26,28 which engage the surface of the tube 2 on opposite sides of the reduced diameter portion 12, and connecting portions 30,32 which extend between the proximal ends of the arms 22,24 on opposite sides of the clip, the connecting portions 30,32 comprising a generally straight centre section from which respective end sections project to the arms 22,24 (FIG. 3).

The second part 16 of the clip comprises a generally U-shaped aluminium strip which passes around the transponder 10 and clips around the outer edges of the straight central sections of the two connecting portions 30,32, such that the transponder is held against the undersides of the straight central sections of the two connecting portions, spaced from the surface of the tube 2.

The window 34 formed between the two connecting portions 30,32 allows the transponder 10 to be read and/or programmed by an external device.

By mounting the transponder to the tube by means of a clip, it will be appreciated that the transponder may be removed from the tube prior to analysis to prevent it from becoming damaged as the tube is heated.

However, by mounting the transponder at the opposite end of the tube to that which is to be heated during analysis and by arranging the clip such that thermal conduction between the tube and the transponder is minimised, the transponder may, if necessary, remain attached to the sampling tube 2 during analysis.

In the latter case, it will further be appreciated that the two-part clip arrangement 14,16 of the present invention allows a transponder which may have become damaged during analysis to be readily replaced by un-clipping the second part 16 of the clip from the first part 14.

The arrangement thus described provides a convenient means for labelling a tube containing an atmospheric sample.

What is claimed is:

1. A sampling device, comprising:
   a transponder;
   an elongate tube having a reduced diameter portion situated toward a first end of said elongate tube, and a second end, said second end of said elongate tube being opposite said first end and being capable of being heated during an analysis without damaging said transponder;
   a clip; and,
   an identification device including said transponder, said transponder being removably attached to said elongate tube via said clip, with said clip being attached within said reduced diameter portion of said elongate tube for inhibiting movement of said identification device along a length of said elongate tube.

2. The sampling device according to claim 1, wherein said transponder is attached to said elongate tube so that said transponder does not directly contact an exterior surface of said elongate tube.

3. The sampling device according to claim 1, wherein said clip comprises a first part for attaching to said elongate tube and a second part for attaching said transponder to said first part.

4. The sampling device according to claim 1, wherein said clip is formed from a material having a low thermal conductivity.

5. The sampling device according to claim 1, wherein elements comprising the sampling tube are formed from glass.

6. The sampling device according to claim 1, wherein elements comprising the sampling tube are formed from a metallic material.

7. A sampling device, comprising:
   an elongate tube;
   a transponder;
   a clip having a first part for attaching to said elongate tube and a second part for attaching said transponder to said first part;
   an identification device including said transponder removably attached-to said elongate tube via said clip, wherein said first part of said clip comprises a pair of resilient arms for engaging opposite sides of said elongate tube and two connecting portions extending between said pair of resilient arms at spaced apart points along an axis of said elongate tube, said second part of said clip comprising a substantially U-shaped member for clipping around said transponder and said two connecting portions of said first part of said clip for holding said transponder against under-sides of said two connecting portions.

8. The sampling device according to claim 7, wherein said pair of resilient arms are arcuate and engage sides of a cylindrical tube.

9. The sampling device according to claim 7, wherein said transponder is attached to said elongate tube so that said transponder does not directly contact an exterior surface of said elongate tube.

10. The sampling device according to claim 7, wherein said clip comprises a first part for attaching to said elongate tube and a second part for attaching said transponder to said first part.

11. The sampling device according to claim 7, wherein said clip is formed from a material having a low thermal conductivity.

12. The sampling device according to claim 7, wherein elements comprising the sampling tube are formed from glass.

13. The sampling device according to claim 7, wherein elements comprising the sampling tube is formed from a metallic material.

14. An identification device, comprising:
   a transponder; and,
   a clip for attaching said transponder to an elongate sampling tube, said clip comprising a first part for attaching to the elongate tube and a second part for attaching said transponder to said first part, wherein said first part of said clip comprises a pair of resilient arms for engaging opposite sides of the elongate tube and two connecting portions extending between said pair of resilient arms at spaced apart points along an axis of the elongate tube, said second part of said clip comprising a substantially U-shaped member for clipping around said transponder and said two connecting portions of said first part of said clip for holding said transponder against undersides of said two connecting portions.

15. The identification device according to claim 14, wherein said pair of resilient arms are arcuate for engaging sides of a cylindrical tube.

16. The identification device according to claim 14, wherein at least said first part of said clip is formed from a material having a low thermal conductivity.

17. The identification device according to claim 14, wherein said clip is formed from a material having a low thermal conductivity.

18. The identification device according to claim 14, wherein said transponder is attached to the elongate tube so that said transponder does not directly contact an exterior surface of the elongate tube.

19. A method for labelling a sampling tube, comprising the step of:
   removably attaching a transponder to an elongate tube via a clip, with the clip being attached within a reduced diameter portion of the elongate tube for inhibiting movement of an identification device along a length of the elongate tube, with the reduced diameter portion of the elongate tube being situated along a first end of the elongate tube so that a second end of the elongate tube, the second end being opposite the first end of the elongate tube, is capable of being heated during analysis without damaging the transponder.

20. The method for labelling a sampling tube according to claim 19, wherein the transponder is attached to the elongate tube so that the transponder does not directly contact an exterior surface of the elongate tube.

21. The method for labelling a sampling tube according to claim 19, wherein the clip comprises a first part for attaching to the elongate tube and a second part for attaching the transponder to the first part of the clip.

22. The method for labelling a sampling tube according to claim 19, wherein the clip is formed from a material having a low thermal conductivity.

23. The method for labelling a sampling tube according to claim 19, wherein at least said first part of said clip is formed from a material having a low thermal conductivity.

24. The method for labelling a sampling tube according to claim 19, wherein the sampling tube is formed from glass.

25. The method for labelling a sampling tube according to claim 19, wherein the sampling tube is formed from a metallic material.

26. A method for labelling a sampling tube, comprising the step of:

removably attaching a transponder to an elongate tube via a clip, with the clip comprising a first part for attaching to the elongate tube and a second part for attaching the transponder to the first part of the clip, the first part including a pair of resilient arms for engaging opposite sides of the elongate tube and two connecting portions extending between the pair of resilient arms at spaced apart points along an axis of the elongate tube, the second part of the clip comprising a substantially U-shaped member for clipping around the transponder and the two connecting portions of the first part of the clip for holding the transponder against undersides of the two connecting portions.

27. The method for labelling a sampling tube according to claim 26, wherein the resilient arms are arcuate for engaging side of a cylindrical tube.

28. The method for labelling a sampling tube according to claim 26, wherein the transponder is attached to the elongate tube so that the transponder does not directly contact an exterior surface of the elongate tube.

29. The method for labelling a sampling tube according to claim 26, wherein the clip comprises a first part for attaching to the elongate tube and a second part for attaching the transponder to the first part of the clip.

30. The method for labelling a sampling tube according to claim 26, wherein the clip is formed from a material having a low thermal conductivity.

31. The method for labelling a sampling tube according to claim 26, wherein at least said first part of said clip is formed from a material having a low thermal conductivity.

32. The method for labelling a sampling tube according to claim 26, wherein the sampling tube is formed from glass.

33. The method for labelling a sampling tube according to claim 26, wherein the sampling tube is formed from a metallic material.

* * * * *